United States Patent
Johansson et al.

(10) Patent No.: US 8,170,649 B2
(45) Date of Patent: May 1, 2012

(54) ARRANGEMENT AND METHOD FOR ASSESSING TISSUE QUALITIES

(75) Inventors: Anders Johansson, Linkoping (SE); Tommy Sundqvist, Linköping (SE); Åke Öberg, Ljungsbro (SE)

(73) Assignee: BioOptico, AB, Linkoping (SE)

( * ) Notice: Subject to any disclaimer, the term of this patent is extended or adjusted under 35 U.S.C. 154(b) by 500 days.

(21) Appl. No.: 10/587,490

(22) PCT Filed: Jan. 27, 2005

(86) PCT No.: PCT/SE2005/000103
§ 371 (c)(1),
(2), (4) Date: Oct. 4, 2006

(87) PCT Pub. No.: WO2005/020290
PCT Pub. Date: Aug. 4, 2005

(65) Prior Publication Data
US 2007/0179381 A1    Aug. 2, 2007

(30) Foreign Application Priority Data

Jan. 27, 2004  (SE) .................................. 0400145

(51) Int. Cl.
*A61B 6/00*   (2006.01)
(52) U.S. Cl. ........ 600/476; 600/587; 600/547; 600/472; 356/39; 356/338; 356/369
(58) Field of Classification Search .................. 600/473, 600/476, 477, 478
See application file for complete search history.

(56) References Cited

U.S. PATENT DOCUMENTS

| | | | | |
|---|---|---|---|---|
| 5,280,788 | A * | 1/1994 | Janes et al. | 600/476 |
| 5,305,759 | A * | 4/1994 | Kaneko et al. | 600/476 |
| 6,091,984 | A | 7/2000 | Perelman et al. | |
| 6,390,978 | B1 * | 5/2002 | Irion et al. | 600/437 |
| 6,437,856 | B1 | 8/2002 | Jacques | |
| 6,624,890 | B2 * | 9/2003 | Backman et al. | 356/369 |
| 6,660,001 | B2 | 12/2003 | Gregory | |
| 2001/0056237 | A1 * | 12/2001 | Cane et al. | 600/475 |
| 2003/0040668 | A1 | 2/2003 | Kaneko et al. | |

(Continued)

FOREIGN PATENT DOCUMENTS
EP    1201182 A2    5/2002

OTHER PUBLICATIONS

Pastoreau et al (Quantitative assessment of articular and subchondral bone histology in the meniscectomized guinea pig model of osteoarthritis, 2003).*

(Continued)

*Primary Examiner* — Tse Chen
*Assistant Examiner* — Joel F Brutus
(74) *Attorney, Agent, or Firm* — Porter Wright Morris & Arthur LLP (57) ABSTRACT

An arrangement and method for imaging and/or measuring tissue qualities, such as tissue thickness, tissue surface roughness and degree of tissue fiber linearization. The arrangement includes at least one light generating element, at least one light detecting element, a probe with an extension, and possibly a control apparatus including a signal processor for processing the detected signals and/or images. The extension is designed to convey light from the light generating element to the tissue for visualization and/or measurement. The extension is also designed to convey light back-scattered from the tissue to the light detecting element. The detecting element is designed to measure the intensity and/or spatial distribution of light back-scattered from the tissue.

26 Claims, 5 Drawing Sheets

U.S. PATENT DOCUMENTS

6,370,422 B1 * 4/2002 Richards-Kortum et al. 600/478

OTHER PUBLICATIONS

Johansson et al., Assessment of cartilage thickness utilising reflectance spectroscopy; Proceedings of the 12th Nordic-Baltic Conference on Biomedical Engineering; Reykjavik, Iceland; 2002.

Johansson et al., Characterisation of the cartilage/bone interface utilising reflectance spectroscopy; Proceedings of the 23rd Annual International Conference of the IEEE Engineering in Medicine and Biology Society; Istanbul, Turkey; 2001.

* cited by examiner

ARRANGEMENT AND METHOD FOR ASSESSING TISSUE QUALITIES

TECHNICAL FIELD

The present invention generally relates to an arrangement and a measurement method for assessing tissue qualities. More specifically, the present invention relates to an arrangement and a method for measuring tissue thickness, tissue surface roughness and degree of tissue fiber linearization. The arrangement comprises a probe and means for light source driving/control, light detection, signal processing and presentation.

PRIOR ART

Endoscopic techniques have been used for the diagnosis and therapy of disorders since the beginning of the twentieth century. One typical example is arthroscopy, where the interior of a joint is visualized. Takagi (TAGAKI, 1918, in ALTMAN and KATES, 1983) modified a pediatric cytoscope to fit the problem area of knee joint visualization, which became the birth of this dynamic and rewarding field. The arthroscope is primarily a diagnostic device but therapeutic variants allow the removal of adhesions, intra-articular debris and meniscectomy (JACKSON, 1983). The arthroscope gives visual information from the interior of a joint. Demands have been raised, though, that a more quantitative approach in diagnostic work would improve the quality of therapeutic decisions. Thickness of cartilage, cartilage surface roughness and the degree of cartilage linearization are all parameters of great interest in a more quantitative approach to cartilage diagnostics.

Many researchers have earlier suggested ways for cartilage thickness assessment. Several of the methods suggested require a disarticulation of the joint. Usually, these methods measure the undeformed thickness of the cartilage layer. Armstrong and Mow (ARMSTRONG and MOW, 1982) developed an optical method, applied to an isolated cartilage/bone specimen, in which the cartilage/bone interface was easily detected. Needle probe methods (HOCH et al., 1983; MOW et al., 1989; RASANEN et al., 1990) measure force and displacement of a sharp needle penetrating the cartilage layer from which cartilage thickness can be calculated. The needle method does not require an isolated specimen, and in situ surfaces can be tested. Jurvelin (JURVELIN et al., 1995) has compared microscopy based measurements, the needle probe method and the ultrasound technique. The linear correlation coefficient between microscopy and the needle probe measurements was 0.97 (n=80) and 0.91 (n=45) between microscopy and ultrasonic measurements. Strong correlation was also obtained between the needle probe measurements and the ultrasonic measurements. The difference between the three methods is of the order of 0.1 mm or less at a mean sample thickness of 0.86 mm. The authors conclude that the three different techniques for cartilage thickness measurements are highly related.

In situ cartilage thickness has also been measured with high resolution ultrasound (MODEST et al., 1989; RUSHFELDT et al., 1981). Wayne (WAYNE et al., 1998) utilized a radiographic and image analyzing method for thickness studies in articulated joints. Swann and Seedhom (SWANN and SEEDHOM, 1989) described an improved needle technique for thickness measurements. These authors all question the methods which disrupt the cartilage layer because of the thickness changes caused by dehydration or hydrophilic swelling. However, the authors report an accuracy of ±0.012 mm with a repeatability of 1.2% for the needle probe.

Optical coherence tomography (OCT) has recently been suggested as a tool to assess articular cartilage structure and thickness (HERRMANN et al., 1999; DREXLER et al., 2000). OCT is based on interferometry between light from a scanning mirror and the cartilage sample. Hermann et al. report resolutions of 5-15 µm and differences between OCT and histological measurements of the order of 7-9%. Drexler et al. suggest that polarization sensitive OCT (PSOCT) can be advantageous for the quantification of collagen structure changes, associated with osteoarthritis. Magnetic resonance imaging (MRI) has been increasingly used to assess articular cartilage injuries and arthritis. In vitro bovine knees have been examined with MRI (MAH et al., 1990). Signal variations have been noticed in degenerated cartilage (LEHNER et al., 1989). MRI has also been used in vivo in a canine arthritis model (BRAUNSTEIN et al., 1990). These studies showed hypertrophic articular cartilage repair and other changes associated with osteoarthritis. MRI has also been used increasingly in human studies (for a review see RECHT and RESNICK, 1994). Many of the studies in humans are knee studies with a focus on the identification of focal defects and cartilage thickness. In these studies the arthroscopy method is often referred to as the gold standard. Roentgenological techniques have also been used for cartilage studies. Double-contrast techniques (HALL and WYSHAK, 1980) have been frequently used in thickness studies in relation to sex, weight and height.

Reflection spectroscopy is a well-established method for investigation of the structural/molecular composition of a tissue volume. Light from a broad band light source is brought to impinge on the tissue. The light is absorbed and scattered in the tissue volume. The detected spectral distribution of diffusely scattered light carries information about the molecular/structural composition of the tissue passed by the photons.

Cartilage behaves spectroscopically almost like a sheet of white paper whereas the underlying bone has a very different reflection spectrum. The differences can partly be explained by the hemoglobin content of bone. Bone is perfused with blood as opposed to cartilage, which is nutritionally supported from the joint liquor.

The source of inspiration to the present work is the clinically expressed demand to perform measurements of cartilage thickness and fiber structure during arthroscopic assessments of joints without disrupting the cartilage layer. An optical method for this purpose would be easily combined with, or integrated into, an arthroscope that would permit simultaneous conventional arthroscopic investigations with quantitative measurements. In a longer perspective, it is probably possible to utilize optical fiber measurements for a variety of other important properties such as bone perfusion, cartilage surface topology and degree of collagen fiber linearization (NÖTZLI et al., 1989; HANDLEY et al., 1990; DREXLER et al., 2000).

SUMMARY OF THE INVENTION

The invention described is an optical device for assessing tissue qualities, based on the differences in optical properties between tissues. The described device provides illumination of the tissue under investigation and back-scattered light is analyzed by a signal processor. According to described procedures, the thickness of a tissue layer in a layered tissue structure is determined by studying intensity quotas for selected wavelengths, and the degree of tissue fiber linearization is determined by studying the intensity of reflected polarized light. Several solutions are presented, including single point measurement, imaging, ocular and miniaturized measurement systems. By the expression "comprising" in the claims we understand including but not limited to.

DETAILED DESCRIPTION

Tissue Layer Thickness Measurement—Materials and Methods

Twelve hip joint condyles from bovine calves were obtained from a local slaughterhouse less than 24 hours after sacrifice. Two of the condyles were used for reference measurements and the other ten for thickness experiments. The condyles were stored in saline in a refrigerator and prepared for cartilage measurements through the removal of soft tissues and tendons surrounding the joint. Three sites on each condyle surface were used for the measurements. A handheld, rotating, grinding machine was used to reduce the cartilage layer thickness. Sandpaper with the roughness P100 was used for grinding. Care was taken to grind in short episodes (5-15 s) so as not to increase the temperature of the cartilage. Thickness measurement of the cartilage layer was done with a high-resolution ultrasound scanner (B-mode 20 MHz, Dermascan 3v3, Cortex Technology, Hadsund, Denmark). The probe scanned over the measurement site and an image of the cartilage/bone interface was presented on the computer screen.

Optical reflection spectra were recorded by using an Oriel Instaspec IV CCD spectrometer equipped with an Ocean Optics broad spectrum tungsten lamp HL 2000 (spectral range 360-2000 nm). The light was guided by optical glass fiber bundles (NA=0.35) and the measurements were taken at a small distance (2-5 mm) to the condyle surface. The bundles were arranged in a probe head (diameter 4 mm) with the emitting fiber bundle encircling the detecting bundle. The reflection spectra were calculated according to the formula:

$$I(\lambda) = \frac{I_{tissue} - I_{background}}{I_{reference} - I_{background}} \quad (1)$$

where $I_{tissue}$ is the raw spectrum of the examined tissue, $I_{background}$ the detector background signal, and $I_{reference}$ the diffuse reflectance spectrum taken from a white reference ($BaSO_4$).

For each measurement position, spectra and ultrasound images were recorded from the intact cartilage layer, for 4-5 intermediate cartilage thicknesses (obtained by grinding) and when bone level had been reached.

Twenty-three pieces of pure cartilage, about 1 mm thick, were removed from the two joints by using a sharp knife. Remains of subchondral bone were carefully removed to secure a pure cartilage sample. Reflection spectra were measured, with the equipment described above, for each piece of cartilage placed on a black plastic sheet. The joints were cut in half, washed in saline and stored (in saline) for a few days to remove remains of blood. Finally, reflection spectra were taken from 10 positions on the exposed bone samples. Mean reference spectra for cartilage (n=23) and bone (n=10) were calculated and will be referred to as $S_{cartilage}$ and $S_{bone}$, respectively. Furthermore, the reference spectrum of blood ($S_{blood}$) was estimated as the inverse absorption spectrum of oxyhemoglobin, taken from the literature (TAKATANI and GRAHAM, 1979). To decrease the influence of remains of blood in the bone, $S_{bone}$ was adjusted by subtracting $S_{blood}$ until the characteristic hemoglobin peaks could no longer be distinguished.

Each measured reflectance spectrum was matched to the true cartilage thickness (d), as determined from the stored ultrasound images. For the thickness determination, the manufacturer's software including a cursor system was used. The resolution of the ultrasound image was 0.06 mm. As a measure of cartilage thickness, determined from the spectroscopic data, $d_{spec}$ was defined as the percentage contribution (%) of cartilage spectrum in the measured reflectance spectrum:

$$d_{spec} = \frac{a}{a+b+c} \quad (2)$$

where a, b and c are the coefficients for optimal match (least square fitting) between the measured spectrum ($S_{measured}$) and the reference spectra according to:

$$S_{measured} = a \cdot S_{cartilage} + b \cdot S_{bone} + c \cdot S_{blood} \quad (3)$$

An exponential regression model (4) was used for statistical comparison between reference cartilage thickness and $d_{spec}$.

$$d_{spec} = K_1 (1 - e^{-K_2 \cdot d}) \quad (4)$$

where $K_1$ and $K_2$ are constants.

Figure 1:
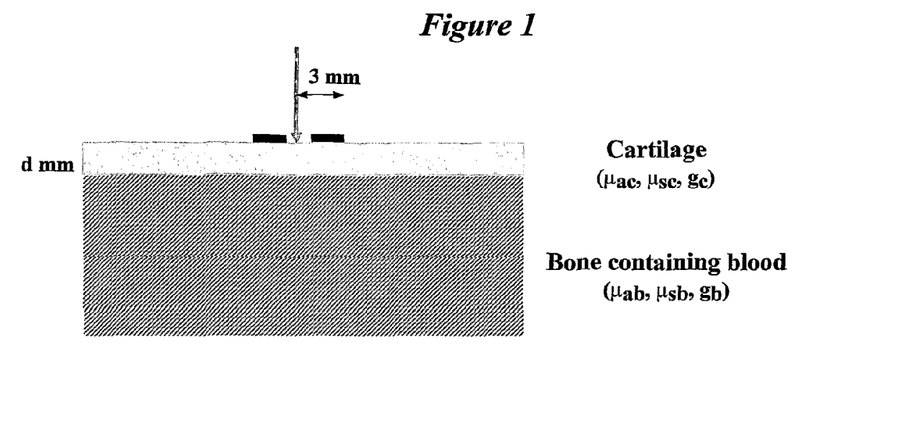
FIG. 1 is the Monte Carlo model used for simulations including a cartilage layer of known thickness (d) on top of a bone layer containing blood. The number of photons (out of incident $10^6$) back-scattered to a ring shaped detector with a radius of 3 mm is calculated.

In order to test the assumption of an exponential relation between the cartilage thickness d and the corresponding spectroscopic data, a Monte Carlo model (DE MUL et al., 1995) was used (FIG. 1). The model has a cartilage layer of known thickness (d) and diffusion theory optical properties ($\mu_{ac}$, $\mu_{sc}$, $g_c$) positioned on top of a semi-infinite layer of bone containing blood ($\mu_{ab}$, $\mu_{sb}$, $g_b$). The optical properties of cartilage, bone and blood were taken from the literature (BEEK et al., 1997; FIRBANK et al., 1993; TUCHIN, 2000) for the single wavelength 633 nm. The optical properties of bone containing blood were set to the bone coefficients increased by those of blood at a selected perfusion level (10%) according to:

$$\mu_{ab} = \mu_{a,bone} + 0.10 \cdot \mu_{a,blood} \quad (5.1)$$

$$\mu_{sb} = \mu_{s,bone} + 0.10 \cdot \mu_{s,blood} \quad (5.2)$$

$$g_b = g_{bone} + 0.10 \cdot (g_{blood} - g_{bone}) \quad (5.3)$$

All optical parameters are presented in Table 1. Refractive indices of both layers were set to 1 as specular effects were not of interest. The pathways of $10^6$ photons, incident in a point at the cartilage surface, were calculated (DE MUL et al., 1995). The back-scattered photons reaching a ring shaped detector (outer radius 3 mm, inner radius 1 mm) were counted. Simulations were performed for cartilage thicknesses d=0-3 mm in steps of 0.1 mm.

TABLE 1

Tissue optical properties used in the Monte Carlo simulations

| | Absorption coefficient $\mu_a$ [mm$^{-1}$] | Scattering coefficient $\mu_s$ [mm$^{-1}$] | Anisotropy factor g |
|---|---|---|---|
| Cartilage | 0.033 | 21.4 | 0.909 |
| Bone | 0.040 | 35.0 | 0.925 |
| Blood | 1.60 | 413 | 0.997 |
| Bone containing blood | 0.20 | 76.3 | 0.932 |

Tissue Linearization Measurement—Materials and Methods

As a model, we used collagen on glass plates. Two samples were polymerized, one inside a strong magnetic field (giving rise to a linearized sample) and another outside of the field (reference sample with randomized fiber directions).

The irradiance transmitted through the samples was studied. A polarized HeNe laser (633 nm) was used as a light source. Transmitted irradiance was recorded during rotation of the linearized sample in 10° steps between 0-360°. This gave rise to a variation in transmitted intensity due to the relative difference between the collagen fiber direction of the sample and the laser polarization plane. The procedure was repeated using the reference sample.

Results

Figure 2:
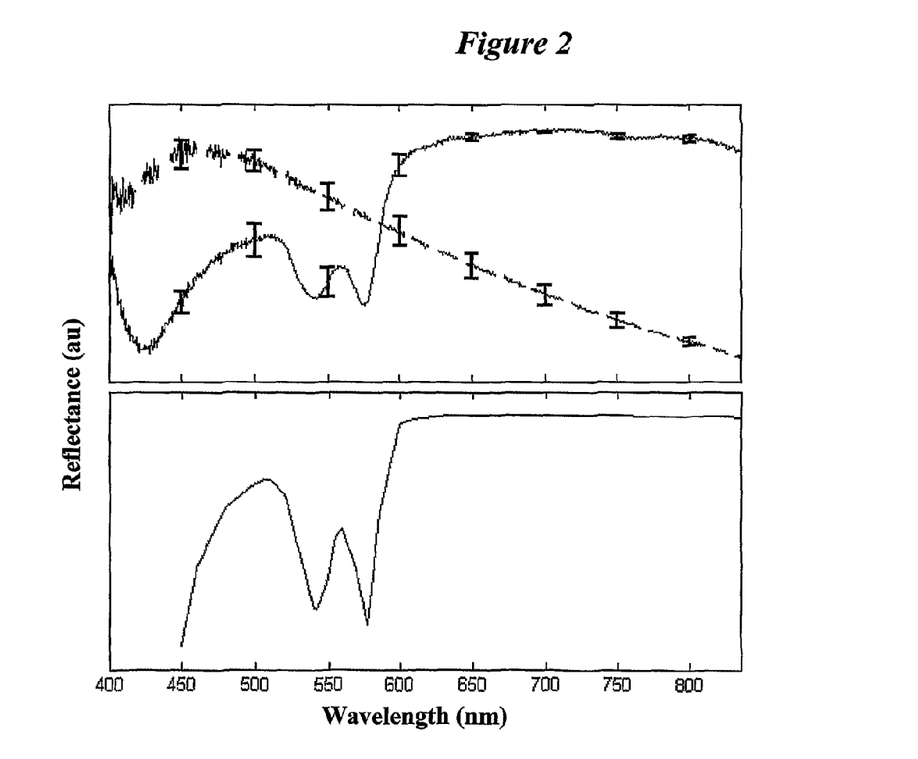
FIG. 2 upper part of figure shows mean reflection spectra from the reference material, including cartilage (dotted line, n=23) and bone containing blood (solid line, n=10). Whiskers show ±SD. Lower part of figure shows reference spectrum of blood (TAKATANI and GRAHAM, 1979).
Figure 3:
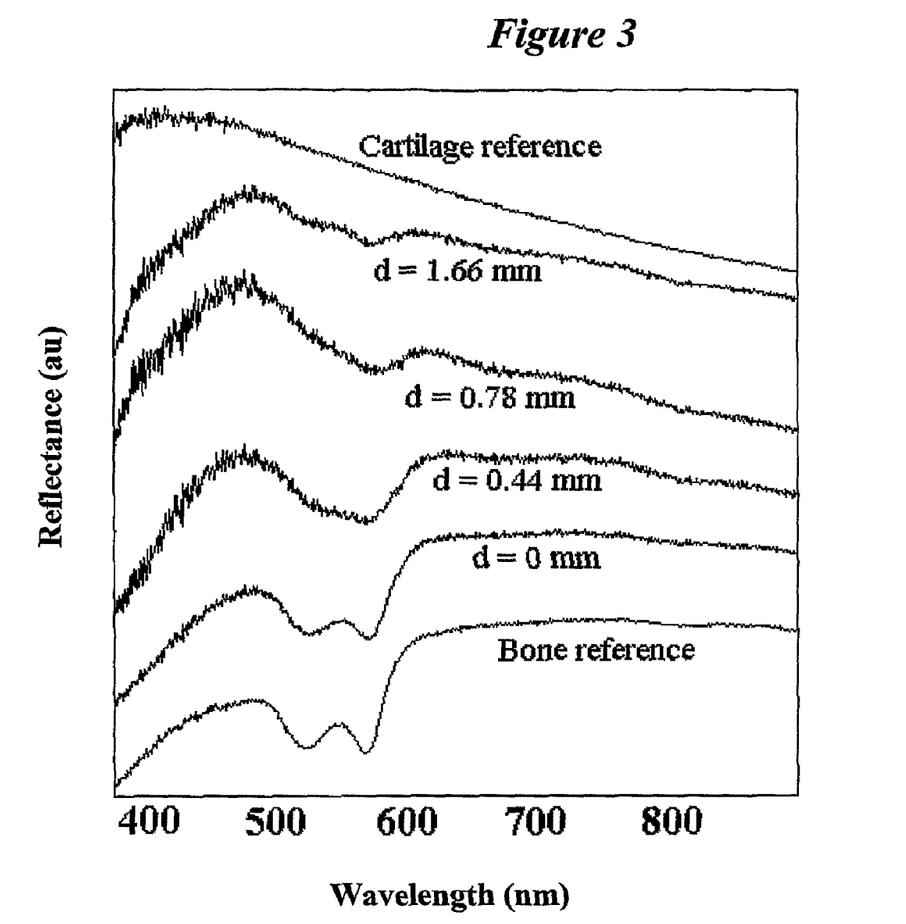
FIG. 3 shows examples of reflectance spectra from a grinding session. Before grinding (d=1.66 mm), after first grinding (d=0.78 mm), after third grinding (d=0.44 mm) and after fourth grinding (d=0 mm). Reference spectra of cartilage and bone containing blood are included for comparison. The spectra are separated in the y-direction for clarity.
Figure 4:
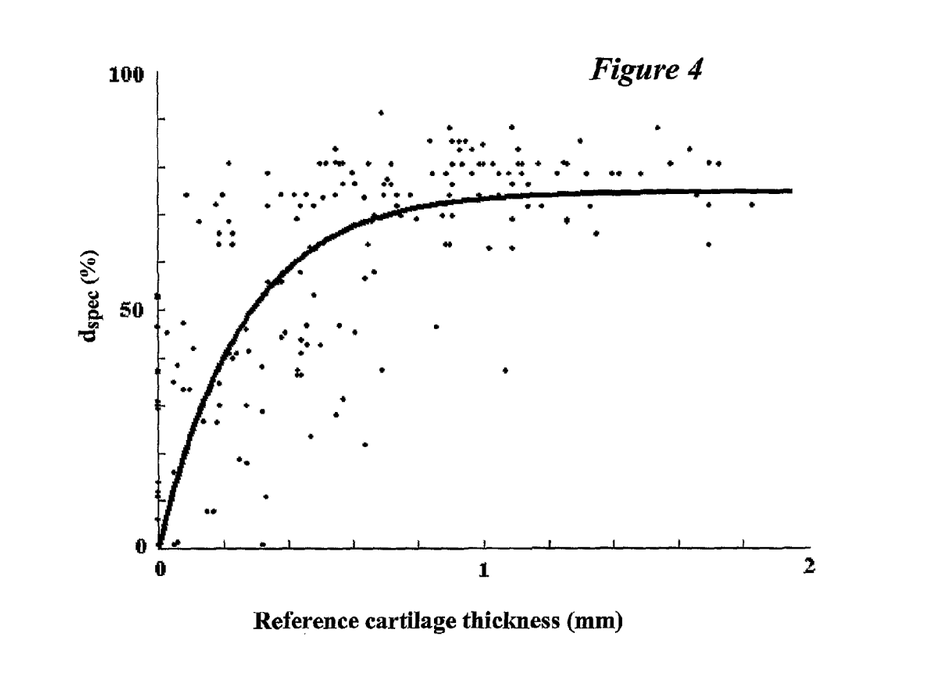
FIG. 4 shows spectroscopically estimated cartilage thickness measure ($d_{spec}$) plotted against reference cartilage thickness for the complete material.

The mean reflection spectra of the reference material are presented in FIG. 2. The cartilage spectrum appears relatively "white" with a shift towards the blue region, whilst the bone spectrum appears distinctly "red" and includes the characteristic absorption peaks of hemoglobin at 542 nm and 576 nm. In the thickness analysis, the latter spectrum is divided into $S_{bone}$ and $S_{blood}$ (see Equation 3). The mean (±SD) thickness of intact cartilage was 1.21±0.30 mm (n=30). A typical example of spectra from a grinding sequence is shown in FIG. 3. As the cartilage layer gets thinner a clear influence of bone can be seen. The spectroscopic estimation of cartilage thickness ($d_{spec}$) is plotted against the ultrasound reference cartilage thickness in FIG. 4. The regression model of Equation 4 is used (r=0.69, p<0.000001, s=0.167, $K_1$=0.75, $K_2$=3.81, n=182). For thinner cartilage layers (d<0.5 mm), the model mean error is 0.19±0.17.

Figure 5:
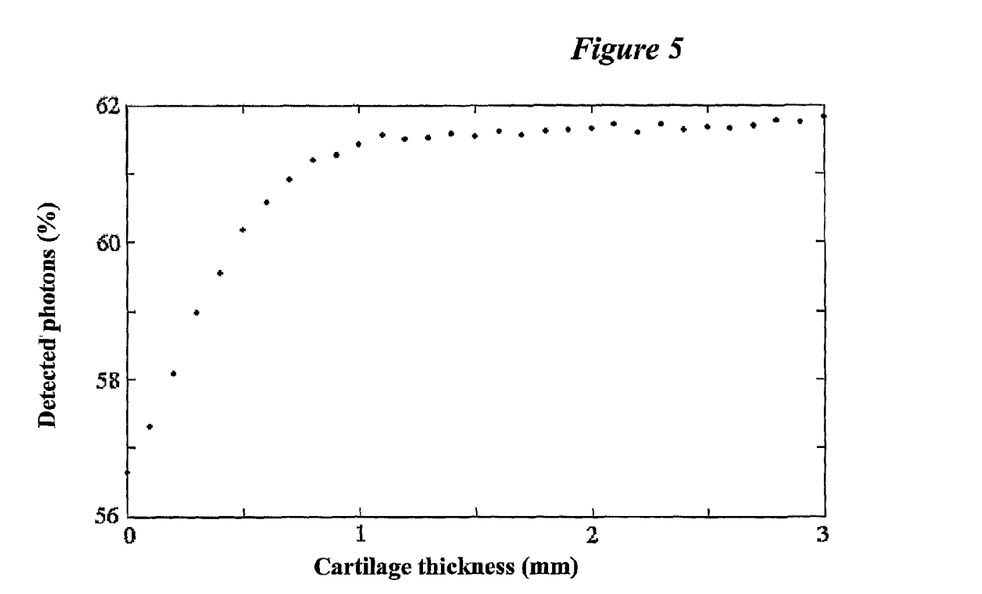
FIG. 5 shows Monte Carlo simulation results, including detected photons out of $10^6$ ejected (in percent) for increasing cartilage layer thicknesses. The simulations are performed for the single wavelength 633 nm.

The Monte Carlo simulation results are presented in FIG. 5. This result is similar to the experimental results in FIG. 4, with more photons reaching the detector at a thicker cartilage layer. The Monte Carlo simulation results support the assumption of an exponential relationship between cartilage thickness and the spectroscopic data.

In the measurements on polymerized collagen, polarized laser light transmission for the linearized sample showed a clear relationship to the angle between laser light polarization plane and collagen fiber direction, with maximum transmission when the two were in parallel. The reference sample showed no such relationship.

Interpretation and Discussion

The main findings in the above study are:
  the possibility to extract objective information about cartilage thickness by studying the reflectance spectrum from the cartilage surface, and
  the possibility to obtain information on collagen fiber linearization by studying polarized light transmission.

These results implicate that it is possible to use a minimally invasive technique to characterize cartilage in connection with in situ diagnosis.

The reflectance spectrum from a condyle surface can be seen as a sum of spectra from cartilage and subchondral bone (containing blood). Typical spectra from cartilage and bone can be seen in FIG. 2. Cartilage contains relatively few cells, which occupy 10-20% of its volume. The remainder is extracellular material, which is highly hydrated and contains up to 80% water by weight. The material consists primarily of large hydrated proteoglycan aggregates, entrapped within a matrix of collagen fibrils. This fiber structure and the fact that absorption of water in the investigated wavelength region is low, gives reason to believe that the character of the cartilage spectrum is an effect of reduced scattering at longer wavelengths according to the Mie theory. Consequently, the cartilage layer acts as a diffuse reflector for photons, impeding them from reaching the highly absorbing subchondral bone.

We intended to assess cartilage thickness by studying the relative content of cartilage and bone components in the combined reflectance spectrum. By using this approach, the accuracy of cartilage thickness determination only becomes dependent upon the variability of the optical properties of these components. This variability remains to be investigated for a larger human material, after which it also will be possible to model the behavior for the complete spectrum and not just for a single wavelength. The exponential relationship between cartilage thickness and diffuse reflectance was expected (NÖTZLI et al., 1989).

A tentative source of error could be the variability of perfusion in the underlying bone. Flow rates in (rabbit) tibial and femoral cortical bone vary in a physiological range of 1.6-7.0 ml·min$^{-1}$·g$^{-1}$ (SHEPHERD and ÖBERG, 1990). Increased perfusion/blood content probably leads to increased absorption by the hemoglobin of the bone. Some of the data scattering in FIG. 4 may be due to the resolution of the ultrasound reference system (0.06 nm according to the manufacturer's specifications). This value can be compared to the model mean error for thinner cartilage layers 0.19±0.17 mm.

The accuracy of the ultrasound reference method depends on the ultrasound speed in cartilage (JURVELIN et al., 1995). Without a calibration of the device to cartilage ultrasound speed data we may have some spreading in data. Grinding causes roughening of the cartilage surface, affecting the degree of specular reflection. However, the specular reflection can be considered wavelength independent, not affecting the thickness estimation, solely based on spectral distribution. For the same reason, the measurement distance was not precisely controlled.

To achieve maximal penetration depth, we chose to record the spectrum between 330-835 nm. It is reasonable to assume that a few characteristic wavelengths can be found that can be used for thickness calculations, thereby eliminating the need for recording the complete spectrum. Such an approach can facilitate the design of an instrument based on the presented principle. An attractive feature of this principle is that it is based on fiber optics. Thus, it can easily be "imbedded" in an arthroscope, which, in addition to the visual assessment of the cartilage surface can give quantitative information about the thickness of the cartilage layer under study. Based on the polarized light transmission results, other important aspects of cartilage quality, such as the linearization and surface roughness, seem possible to extract using optical sensing in an arthroscope.

We found a large variation in the thickness of the bovine hip joint cartilage (0.67-1.98 mm). The same variation can be found in human hip joint cartilage (1.14-2.84 mm), depending on where on the joint the cartilage is measured (NAKANISHI et al., 2001). There are reasons to believe that hip joints or smaller joints can be assessed through the sterile introduction of a fiber optic bundle but the most interesting application for this new principle may be the assessment of the knee via arthroscopy. The cartilage thickness of healthy and osteoarthritic human knee joints varies in the range of 0.5 to 7.4 mm (KLADNY et al., 1999). With the present method the hemoglobin absorption peaks could often be seen for thicker cartilage layers (FIG. 3) but a clear spectral effect occurred at cartilage thicknesses below 0.5 mm. In a well-perfused bone the variation and sensitivity of the method may be improved. Penetration depth may also be improved by focusing on the diffuse reflection component, by using more efficient optical components and by geometrical separation of light source and detector. Blood perfusion of bone has, for instance, been measured at 3.5 mm penetration depth, including penetration of a 1 mm thick cartilage layer, using a 632.8 nm laser Doppler technique (NÖTZLI et al., 1999).

Conclusions

After studying bovine hip joint condyles and polymerized collagen, it was found that information about cartilage thickness and collagen fiber structure can be extracted using optical reflectance spectroscopy and polarized light transmission, respectively. For thicker cartilage layers, a high reflection for the wavelengths 400-600 nm is seen, and for thinner cartilage layers, the characteristic spectra of blood and bone dominate. The opposite is seen for wavelengths in the near infrared region. Linearized collagen shows higher transmission when the polarization plane of the incoming light is parallel with the fiber direction. Consequently, the optical reflectance spectrum may be used to characterize cartilage, and specifically cartilage thickness, in connection with in situ diagnosis. Furthermore, polarization measurement can be used for studying cartilage collagen linearization.

Technical Solution 1

Figure 6:
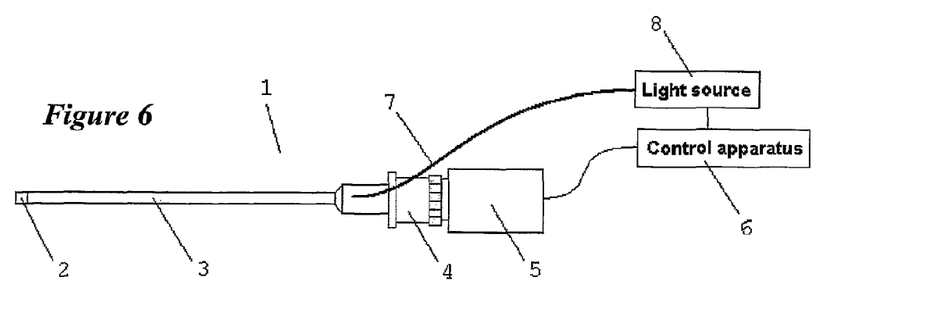
FIG. 6 shows a schematic drawing of a suggested measurement system. Imaging by using white light illumination and signal processing for creating images with enhanced contrast between tissues with different optical properties.

Imaging by using white light illumination and signal processing for creating images with enhanced contrast between tissues with different optical properties. The solution is presented in FIG. 6 and FIG. 7. White light is supplied by light source 1 (8) emitting light into fiber bundle 1 (7). The light source is driven by a light source driver unit (11), controlled by a control unit (10) in a control apparatus (6). Light source 1 (8) could be a broad band tungsten lamp and fiber bundle 1 (7) could consist of high aperture optical glass fibers. Fiber bundle 1 (7) is passing through a channel in the extension (3) of the probe (1) and supplies illumination of the measurement object via a lens (2). This light serves both as illumination for investigation and measurement. In another solution, the fiber bundle 1 (7) is mounted on the extension (3) in a removable fashion. Light reflected from the measurement object is collected via the lens (2) and projected onto a CCD camera (5) via an adapter (4). A CCD camera with enhanced sensitivity in the near-infrared wavelength region could be used. After manual input via an input device (9) in the control apparatus (6), requesting measurement to start, the CCD image is read by the control apparatus (6) and processed in a signal processor (13). The reading could be made continuous. According to the theory presented above, the image should be processed as to increase wavelength information where differences in absorption between the tissue components are seen. These wavelengths could correspond to hemoglobin absorption peaks (5-10 nm in the vicinity of 425, 542 or 576 nm) or water absorption (1000-2000 nm, preferably 1300 nm). Contrast enhanced images of the measurement object are presented on a display unit (12) in the control apparatus (6). The input device (9), control unit (10), signal processor (13) and/or display unit (12) can be that of a computer.

Technical Solution 2

Imaging by discrete wavelength and/or polarized light illumination for creating images with enhanced contrast between tissues with different optical properties and/or between tissues with a linearized and normal fiber structure. The solution is presented in FIG. 7 and FIG. 8. Light source 2 (14) emits white light for illumination for investigation and a number of discrete wavelengths for measurement. The white light source could be a broad band tungsten lamp and the discrete wavelength light sources could be light emitting diodes. Wavelengths emitted from said discrete wavelength light sources could correspond to hemoglobin (5-10 nm in the vicinity of 425, 542 or 576 nm) or water absorption (1000-1600 nm, preferably 1300 nm). In one solution, light source 2 (14) is replaced by a single white light source. An optical filter extracts discrete wavelengths for measurement and the unfiltered white light is used for illumination for investigation. The optical filter could be a liquid crystal filter. Light source 3 (15) with a polarization filter (16) is used for a separate channel. This light source could be a broad band tungsten lamp. In one solution light source 2 (14) is used for both channels and light source 3 (15) becomes redundant. Both light source 2 (14) and light source 3 (15) are driven by a light source driver unit (11), controlled by a control unit (10) in a control apparatus (6). The light from light source 2 (14) is emitted into fiber bundle 1 (7). This fiber bundle could consist of high aperture optical glass fibers. The light from light source 3 (15) is emitted into fiber bundle 2 (17). This fiber bundle could consist of polarization maintaining optical glass fibers. In another solution high aperture optical glass fibers are used and the polarization filter (16) is positioned at the distal end of the extension (3) of the probe (1). Both fiber bundle 1 (7) and fiber bundle 2 (17) pass through a channel in the extension (3) of the probe (1) and supply illumination of the measurement object via a lens (2). The light from fiber bundle 1 (7) serves both as illumination for investigation and measurement. In another solution, fiber bundle 1 (7) and/or fiber bundle 2 (17) is mounted on the extension (3) of the probe (1) in a removable fashion. Light reflected from the measurement object is collected via the lens (2) and projected onto a CCD camera (5) via an adapter (4). A CCD camera with enhanced sensitivity in the near-infrared wavelength region could be used. After manual input via an input device (9) in the control apparatus (6), requesting measurement to start, the CCD image is read by the control apparatus (6) and processed in a signal processor (13). The reading could be made continuous. According to the theory presented above, images enhancing contrast between tissue components with different optical properties are obtained during discrete wavelength illumination by light source 2 (14), and images enhancing contrast between tissues with a linearized and normal fiber structure are obtained during polarized light illumination by light source 3 (15). Contrast enhanced images of the measurement object are presented on a display unit (12) in the control apparatus (6). The input device (9), control unit (10), signal processor (13) and/or display unit (12) can be that of a computer.

Technical Solution 3

Visualization based on discrete wavelength and/or polarized light illumination for enhancing contrast between tissue components with different optical properties and/or between tissues with a linearized and normal fiber structure. The solution is presented in FIG. 7 and FIG. 9. Light source 2 (14) emits white light for illumination for investigation and a number of discrete wavelengths for measurement.

Figure 7:
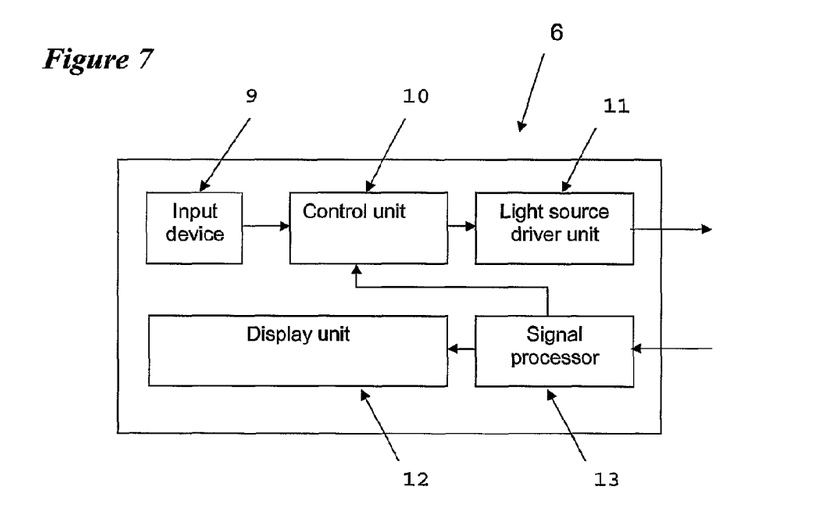
FIG. 7 shows a schematic drawing of the control apparatus of the measurement systems in FIG. 6 and FIG. 8-FIG. 11.
Figure 8:
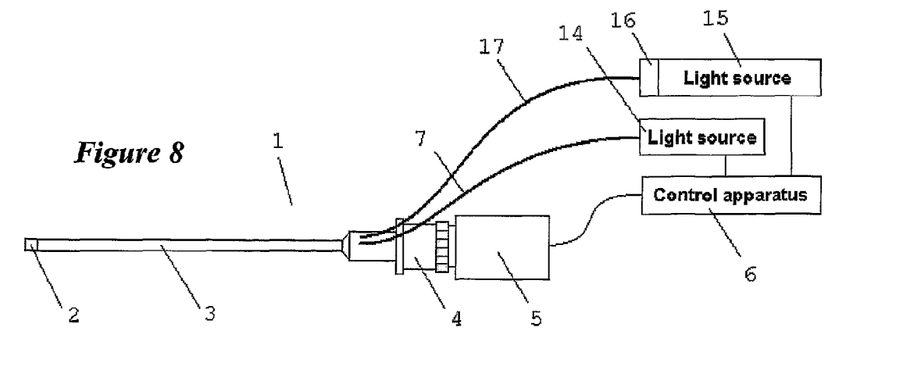
FIG. 8 shows a schematic drawing of a suggested measurement system. Imaging by discrete wavelength and/or polarized light illumination for creating images with enhanced contrast between tissues with different optical properties and/or between tissues with a linearized and normal fiber structure.
Figure 9:
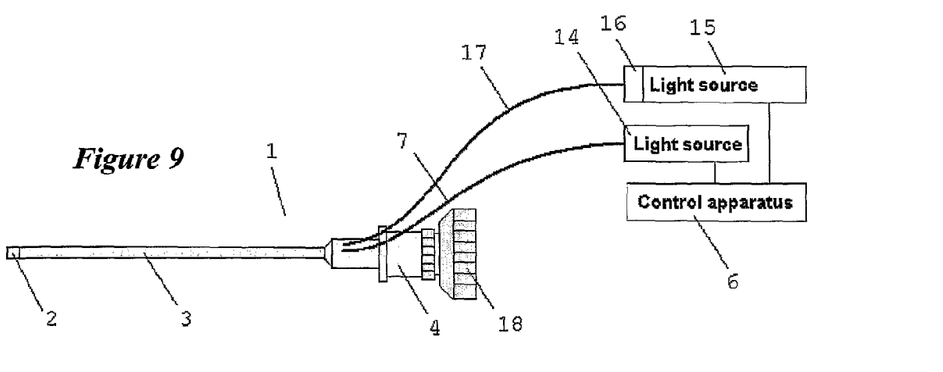
FIG. 9 shows a schematic drawing of a suggested measurement system. Ocular visualization based on discrete wavelength and/or polarized light illumination for enhancing contrast between tissues with different optical properties and/or between tissues with a linearized and normal fiber structure.

The white light source could be a broad band tungsten lamp and the discrete wavelength light sources could be light emitting diodes. Wavelengths emitted from said discrete wavelength light sources could correspond to hemoglobin (5-10 nm in the vicinity of 425, 542 or 576 nm) or water absorption (1000-1600 nm, preferably 1300 nm). In one solution, light source 2 (14) is replaced by a single white light source. An optical filter extracts discrete wavelengths for measurement and the unfiltered white light is used for illumination for investigation. The optical filter could be a liquid crystal filter. Light source 3 (15) with a polarization filter (16) is used for a separate channel. This light source could be a broad band tungsten lamp. In one solution light source 2 (14) is used for both channels and light source 3 (15) becomes redundant. Both light source 2 (14) and light source 3 (15) are driven by a light source driver unit (11), controlled by a control unit (10) in a control apparatus (6). The light from light source 2 (14) is emitted into fiber bundle 1 (7). This fiber bundle could consist of high aperture optical glass fibers. The light from light source 3 (15) is emitted into fiber bundle 2 (17). This fiber bundle could consist of polarization maintaining optical glass fibers. In another solution high aperture optical glass fibers are used and the polarization filter (16) is positioned at the distal end of the extension (3) of the probe (1). Both fiber bundle 1 (7) and fiber bundle 2 (17) pass through a channel in the extension (3) of the probe (1) and supply illumination of the measurement object via a lens (2). In another solution, fiber bundle 1 (7) and/or fiber bundle 2 (17) is mounted on the extension (3) of the probe (1) in a removable fashion. Light reflected from the measurement object is collected via the lens (2) and viewed by the observer through an eye-piece (18) via an adapter (4). Measurement is started via an input device (9) in the control apparatus (6). The reading could be made continuous. According to the theory presented above, images enhancing contrast between tissue components with different optical properties are obtained during discrete wavelength illumination by light source 2 (14), and images enhancing contrast between tissues with a linearized and normal fiber structure are obtained during polarized light illumination by light source 3 (15). The input device (9) and/or the control unit (10) can be that of a computer. In this solution (technical solution 3) the signal processor (13) and display unit (12) of the control apparatus (6) become redundant.

Technical Solution 4

Figure 10:
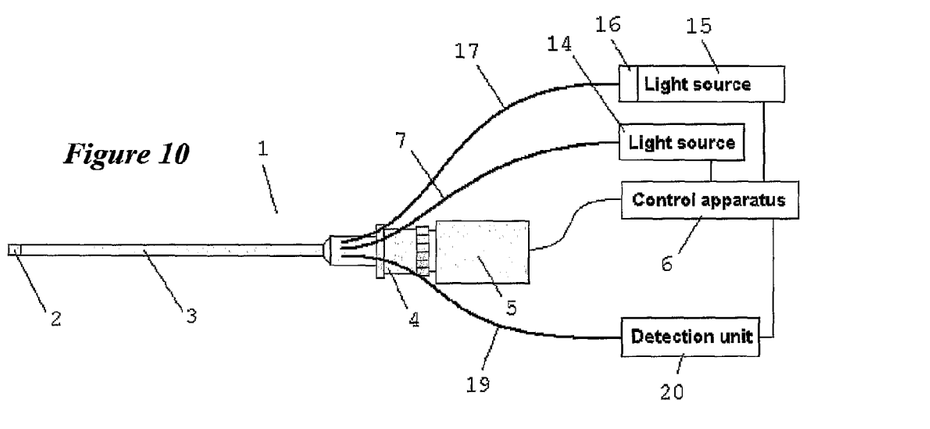
FIG. 10 shows a schematic drawing of a suggested measurement system. Discrete wavelength and/or polarized light illumination for creating images with enhanced contrast between tissues with different optical properties and/or between tissues with a linearized and normal fiber structure, combined with point-wise measurement of tissue layer thickness.

Imaging by discrete wavelength and/or polarized light illumination for creating images with enhanced contrast between tissue components with different optical properties and/or between tissues with a linearized and normal fiber structure, combined with point-wise measurement of tissue layer thickness. The solution is presented in FIG. 7 and FIG. 10. Light source 2 (14) emits white light for illumination for investigation and a number of discrete wavelengths for measurement. The white light source could be a broad band tungsten lamp and the discrete wavelength light sources could be light emitting diodes. Wavelengths emitted from said discrete wavelength light sources could correspond to hemoglobin (5-10 nm in the vicinity of 425, 542 or 576 nm) or water absorption (1000-1600 nm, preferably 1300 nm). A reference wavelength where similar absorption between the tissue components is seen should be used. Said reference wavelength could be in the 600-800 nm region, preferably 630 nm. In one solution, light source 2 (14) is replaced by a single white light source. An optical filter extracts discrete wavelengths for measurement and the unfiltered white light is used for illumination for investigation. The optical filter could be a liquid crystal filter. Light source 3 (15) with a polarization filter (16) is used for a separate channel. This light source could be a broad band tungsten lamp. In one solution light source 2 (14) is used for both channels and light source 3 (15) becomes redundant. Both light source 2 (14) and light source 3 (15) are driven by a light source driver unit (11), controlled by a control unit (10) in a control apparatus (6). The light from light source 2 (14) is emitted into fiber bundle 1 (7). This fiber bundle could consist of high aperture optical glass fibers. The light from light source 3 (15) is emitted into fiber bundle 2 (17). This fiber bundle could consist of polarization maintaining optical glass fibers. In another solution high aperture optical glass fibers are used and the polarization filter (16) is positioned at the distal end of the extension (3) of the probe (1). Both fiber bundle 1 (7) and fiber bundle 2 (17) pass through a channel in the extension (3) of the probe (1) and supply illumination of the measurement object via a lens (2). In another solution, fiber bundle 1 (7) and/or fiber bundle 2 (17) is mounted on the extension (3) in a removable fashion. The light from fiber bundle 1 (7) serves both as illumination for investigation and measurement. Light reflected from the measurement object is collected via the lens (2) and projected onto a CCD camera (5) via an adapter (4). A CCD camera with enhanced sensitivity in the near-infrared wavelength region could be used. Light reflected from a sub-section of the measurement object is collected by fiber bundle 3 (19). This fiber bundle could consist of low aperture optical glass fibers. In another solution, fiber bundle 3 (19) is mounted on the extension (3) of the probe (1) in a removable fashion. The radiation intensity emerging from fiber bundle 3 (19) is measured by a detection unit (20), preferably containing photo diodes. After manual input via an input device (9) in the control apparatus (6), requesting measurement to start, the CCD image is read by the control apparatus (6) and processed in a signal processor (13). The reading could be made continuous. According to the theory presented above, images enhancing contrast between tissue components with different optical properties are obtained during discrete wavelength illumination by light source 2 (14), and images enhancing contrast between tissues with a linearized and normal fiber structure are obtained during polarized light illumination by light source 3 (15). Contrast enhanced images of the measurement object are presented on a display unit (12) in the control apparatus (6). Following sequential illumination by light source 2 (14), the signal processor (13) calculates quotas between the intensities of measurement and reference wavelengths as measured by the detection unit (20). The calculated quotas are translated by the signal processor (13) to tissue layer thicknesses according to the theory presented above, and the tissue layer thickness is presented on the display unit (12) in the control apparatus (6). The input device (9), control unit (10), signal processor (13) and/or display unit (12) can be that of a computer.

Technical Solution 5

Figure 11:
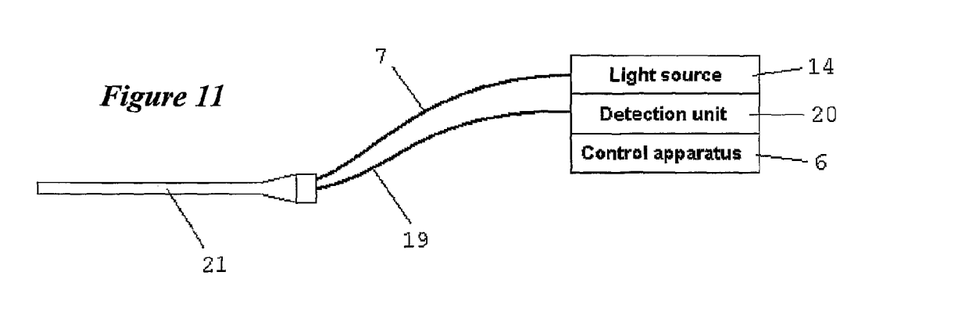
FIG. 11 shows a schematic drawing of a suggested measurement system. Miniaturized device for point-wise measurement of tissue layer thickness.

Miniaturized measurement system for point-wise measurement of tissue layer thickness. The solution is presented in FIG. 7 and FIG. 11. Light source 2 (14) emits a number of discrete wavelengths for measurement. The light sources could be light emitting diodes. Wavelengths emitted from said discrete wavelength tight sources could correspond to hemoglobin (5-10 nm in the vicinity of 425, 542 or 576 nm) or water absorption (1000-1600 nm, preferably 1300 nm). A reference wavelength where similar absorption between the tissue components is seen should be used. Said reference wavelength could be in the 600-800 nm region, preferably 630 nm. In one solution, light source 2 (14) is replaced by a single white light source. An optical filter extracts discrete wavelengths for measurement. The optical filter could be a liquid crystal filter. Light source 2 (14) is driven by a light source driver unit (11), controlled by a control unit (10) in a control apparatus (6). The light from light source 2 (14) is emitted into fiber bundle 1 (7). This fiber bundle could consist of high or low aperture optical glass fibers. Fiber bundle 1 (7) passes through a protective tube (21) and supply illumination of the measurement object. The protective tube (21) is preferably manufactured in a tenable plastic material. Light reflected from the enlightened section of the measurement object is collected by fiber bundle 3 (19). This fiber bundle could consist of high or low aperture optical glass fibers. The radiation intensity emerging from fiber bundle 3 (19) is measured by a detection unit (20), preferably containing photodiodes. The reading could be made continuous. After manual input via an input device (9) in the control apparatus (6), requesting measurement to start, sequential illumination by light source 2 (14) is performed. The signal processor (13) calculates quotas between the intensities of measurement and reference wavelengths as measured by the detection unit (20). The calculated quotas are translated by the signal processor (13) to tissue layer thicknesses according to the theory presented above. The tissue layer thickness is presented on the display unit (12) in the control apparatus (6). The input device (9), control unit (10), signal processor (13) and/or display unit (12) can be that of a computer.

| | |
|---|---|
| 1 | Probe |
| 2 | Lens |
| 3 | Extension |
| 4 | Adapter |
| 5 | CCD camera |
| 6 | Control apparatus |
| 7 | Fiber bundle 1 |
| 8 | Light source 1 |
| 9 | Input device |
| 10 | Control unit |
| 11 | Light source driver unit |
| 12 | Display unit |
| 13 | Signal processor |
| 14 | Light source 2 |
| 15 | Light source 3 |
| 16 | Polarization filter |
| 17 | Fiber bundle 2 |
| 18 | Eye-piece |
| 19 | Fiber bundle 3 |
| 20 | Detection unit |
| 21 | Protective tube |

REFERENCES

ARMSTRONG, C. G., and MOW, V. C. (1982): 'Variations in the intrinsic mechanical properties of human articular cartilage with age, degeneration and water content', *Am. J. Bone Joint Surg.*, 64A, pp. 88-94

BEEK, J. F., BLOKLAND, P., POSTHUMUS, P., et al. (1997): 'In vitro double integrating-sphere optical properties of tissues between 630 and 1064 nm', *Phys. Med. Biol.*, 42, pp. 2255-2261

BRAUNSTEIN, E. M., BRANDT, K. D., and ALBRECHT, M. (1990): 'MRI demonstration of hypertrophic articular repair in osteoarthritis', *Skel. Radiol.*, 19, pp. 335-339

DE MUL, F. F. M., KOELINK, M. H., KOK, M. L., et al. (1995): 'Laser Doppler velocimetry and Monte Carlo simulations on models for blood perfusion in tissue', *Applied Optics*, 34, pp. 6595-6611

DREXLER, W., STAMPER, D., JESSER, C., et al. (2001): 'Correlation of collagen organization with polarization sensitive imaging of in vivo cartilage: Implications for osteoarthritis', *J. Rheumatol*, 28, pp. 1311-18.

FIRBANK, M., HIRAOKA, M., ESSENPREIS, M., and DELPY, D. T. (1993): 'Measurement of the optical properties of the skull in the wavelength range 650-950 nm', *Phys. Med. Biol.*, 38, pp. 503-510

HALL, F. M., and WYSHAK, G. (1980): 'Thickness of cartilage in the normal knee', *J. Bone Joint. Surg.*, 62A, pp. 408-413

HANDLEY, R. C., ESSEX, T., and POOLEY, J. (1990): 'Laser Doppler flowmetry and bone blood flow in an isolated perfusion preparation', *J. Med. Eng. Technol.*, 14, pp. 201-204

HERRMANN, J. M., PITRIS C., BOUMA, B. E., et al. (1999): 'High resolution imaging of normal and osteoarthritic cartilage with optical coherence tomography', *J. Rheumatol.*, 26, pp. 627-635

HOCH, D. H., GRODZINSKY, A. J., KOOB, T. J., et al. (1983): 'Early changes in material properties of rabbit articular cartilage after meniscectomy', *J. Orthop. Res.*, 1, pp. 4-12

JACKSON, R. W. (1983): 'Current concepts review: Arthroscopic surgery', *J. Bone Joint Surg.*, 65, pp. 416-420

JURVELIN, J. S., RÄSÄNEN, T., KOLMONEN, P., and LYYRA, T. (1995): 'Comparison of optical needle probe and ultrasound technique for measurement of articular cartilage thickness', *J. Biomechanics*, 28, pp. 231-235

KLADNY, B., MARCUS, P., SCHIWY-BOCHAT, K.-H., et al. (1999): 'Measurement of cartilage thickness in the human knee-joint by magnetic resonance imaging using a three-dimensional gradient-echo sequence', *International Orthopaedics*, 23, pp. 264-267

LEHNER, K. B., RECHL, H. P., GMENWIESER, J. K., et al. (1989): 'Structure, function and degeneration of bovine hyaline cartilage: assessment with MR imaging in-vitro', *Radiology*, 170, pp. 495-499

MAH, E. T., LANGLOIS, S. P., LOTT, C. W., LEE, W. K., BROWN, G. (1990): 'Detection of articular defects using magnetic resonance imaging: an experimental study', *Aust. N. Z. Surg.*, 60, pp. 977-981

MODEST, V. E., MURPHY, M. C., and MANN, R. W. (1989): 'Optical verification of a technique for in situ ultrasonic measurement of articular cartilage thickness', *J. Biomechanics*, 22, pp. 171-176

MOW, V. C., GIBBS, M. C., LAI, W. M., ZHU, W. B., and ATHANASIOU, K. A. (1989): 'Biphasic indentation of articular cartilage. II—A numerical algorithm and an experimental study', *J. Biomechanics*, 22, pp. 853-861

NAKANISHI, K., TANAKA, H., SUGANO, N., et al. (2001): 'MR-based three-dimensional presentation of cartilage thickness in the femoral head', *Eur. Radiol.*, 11, pp. 2178-83

NÖTZLI, H. P., SWIONTKOWSKI, M. F., THAXTER, S. T., et al. (1989): 'Laser Doppler flowmetry for bone blood flow measurements: Helium-neon laser light attenuation and depth of perfusion assessment', *J. Orthopeadic Res.*, 7, pp. 413-424

RECHT, M. P., and RESNICK, D. (1994): 'MR imaging of articular cartilage: current status and future directions', *AJR*, 163, pp. 283-290

RUSHFELDT, P. D., MANN, R. W., and HARRIS, W. H. (1981): 'Improved techniques for measuring in vitro. The geometry and pressure distribution in the human acetabulun. I—Ultrasonic measurement of acetabular surfaces, sphericity and cartilage thickness', *J. Biomechanics*, 14, pp. 252-260

RASANEN, T., JURVELIN, J., and HELMINEN, H. J. (1990): 'Indentation and shear tests of bovine knee articular cartilage', *Biomech. Sem.*, 5, pp. 22-28

SHEPHERD, A. P., and ÖBERG, P. Å (eds) (1990): 'Laser-Doppler Flowmetry', Kluwer Academic Publishers SWANN, A. C., and SEEDHOM, B. B. (1989): 'Improved technique for measuring the indentation and thickness of articular cartilage', *Proc. Inst. Mech. Eng.*, 203, pp. 143-150

TAGAKI, K. (1918) quoted in ALTMAN, R. D., and KATES, J. (1983): 'Arthroscopy of the knee', *Semin. Arthritis. Rheum.*, 13, pp. 188-199

TAKATANI, S., and GRAHAM, M. D. (1979): 'Theoretical analysis of diffuse reflectance from a two-layer tissue model', *IEEE Trans. Biomed. Eng.*, BME-26, pp. 656-664

TUCHIN, V. (2000): 'Tissue optics—Light scattering methods and instruments for medical diagnosis', *Tutorial texts in optical engineering*, Volume TT38, SPIE Press, Washington, USA WAYNE, J. S., BRODRICK, C. W., and MUKHERIE, N. (1998): 'Measurement of articular cartilage thickness in the articulated knee', *Ann. Biomed. Engng.*, 26, pp. 96-102

All references cited herein are incorporated by reference.

The invention claimed is:

1. A device for measuring the thickness of a layer of cartilage located on subchondral bone, said device comprising:
    at least one light source;
    a probe;
    at least one fiber bundle configured for conveying light from said at least one light source to the surface of the cartilage when said probe is positioned adjacent to the cartilage, without disrupting the surface of the cartilage;
    a light detector; and
    a signal processor configured to determine the thickness of the cartilage based on data acquired by said light detector;
    wherein:
    said at least one light source generates light of known intensity, of a plurality of wavelengths,
    said light detector is configured for measuring the intensity of light back-scattered from the cartilage and the underlying subchondral bone for at least two of said plurality of wavelengths, and
    said signal processor is configured to determine the cartilage thickness based on predetermined optical properties of cartilage and subchondral bone at said at least two wavelengths, and based on the measured intensity of the back-scattered light at said at least two wavelengths.

2. The device according to claim 1 wherein said at least one light source is configured to generate light of said at least two wavelengths which include a reference light wavelength and a measurement light wavelength, wherein said light detector is configured to measure intensities of back-scattered light at said reference light wavelength and said measurement light wavelength, and further wherein said signal processor is configured to compare said measured intensities of back-scattered reference light and measurement light in order to determine the thickness of the cartilage.

3. The device according to claim 2 wherein said light detector is a two-dimensional intensity detector.

4. The device in accordance with claim 3 wherein said two-dimensional intensity detector is a CCD camera.

5. The device in accordance with claim 2 wherein said at least one light source is a white light source for visualization of the cartilage, and said reference light and measurement light wavelengths are extracted from said white light source by a material selected to pass said reference light and measurement light wavelengths.

6. The device in accordance with claim 5 comprising means for multiplexing said reference light and measurement light emitted from said at least one light source.

7. The device in accordance with claim 2 wherein said reference light wavelength is within a wavelength region wherein similar absorption between cartilage and bone is seen.

8. The device according to claim 7 wherein said reference light wavelength is within the 600-800 nm wavelength range.

9. The device in accordance with claim 2 wherein said measurement light wavelength is within a wavelength region wherein differences in absorption between cartilage and bone are seen.

10. The device according to claim 9 wherein said measurement light wavelength is within a wavelength region corresponding to a hemoglobin absorption peak, in the vicinity of 425, 542 or 576 nm, or within a wavelength region with high water absorption.

11. The device according to claim 1 wherein said at least one light source is configured to generate white light, wherein white light from said at least one light source is conveyed through said fiber bundle for illumination of the cartilage, and wherein said signal processor is configured to compare said measured intensities at said at least two wavelengths in order to determine the thickness of the cartilage.

12. The device according to claim 11 wherein said light detector is a two-dimensional intensity detector.

13. The device in accordance with claim 12 wherein said two-dimensional intensity detector is a CCD camera.

14. The device in accordance with claim 11, wherein the wavelength of one of said at least two wavelengths is within a wavelength region where similar absorption between cartilage and bone is seen.

15. The device in accordance with claim 14 wherein said wavelength region is within the 600-800 nm wavelength range.

16. The device in accordance with claim 11, wherein the wavelength of one of said at least two wavelengths is within a wavelength region wherein differences in absorption between cartilage and bone are seen.

17. The device in accordance with claim 16 wherein said wavelength region corresponds to a hemoglobin absorption peak, in the vicinity of 425, 542 or 576 nm, or to a wavelength region with high water absorption.

18. The device in accordance with claim 1 wherein said at least one light source is configured to generate light of at least two wavelengths including a reference light wavelength and a measurement light wavelength, such that said generated light is conveyed through said fiber bundle for illumination of the cartilage, and further wherein the device is configured such that light back-scattered from the cartilage and the underlying subchondral bone is conveyed back to an eye-piece for visual inspection.

19. The device according to claim 18 wherein said at least one light source is configured to generate white light for visualization of the cartilage, and said reference light and measurement light wavelengths are extracted from said white light source by a material selected to pass said reference light and measurement light wavelengths.

20. The device in accordance with claim 19 comprising means for multiplexing said reference light and measurement light emitted from said at least one light source.

21. The device in accordance with claim 18, wherein said reference light wavelength is within a wavelength region where similar absorption between cartilage and bone is seen.

22. The device in accordance with claim 21 wherein said reference light wavelength is within the 600-800 nm wavelength range.

23. The device in accordance with claim 18 wherein said measurement light wavelength is within a wavelength region wherein differences in absorption between cartilage and bone are seen.

24. The device in accordance with claim 23 wherein said measurement light wavelength is within a wavelength region corresponding to a hemoglobin absorption peak, in the vicinity of 425, 542 or 576 nm, or within a wavelength region with high water absorption.

25. A method for measuring the thickness of a layer of cartilage located on subchondral bone, comprising:
   illuminating the surface of the cartilage with light of a plurality of wavelengths, without disrupting the surface of the cartilage;
   measuring the intensity of light back-scattered from the cartilage and the underlying subchondral bone for at least two of said plurality of wavelengths;
   determining cartilage thickness based on predetermined optical properties of cartilage and subchondral bone at said two of more of said plurality of wavelengths, and based on the intensity of the back-scattered light at said two or more of said plurality of wavelengths.

26. The method of claim 25, wherein said step of illuminating the surface of the cartilage with light of a plurality of wavelengths comprises illuminating the cartilage with white light.

\* \* \* \* \*

UNITED STATES PATENT AND TRADEMARK OFFICE
CERTIFICATE OF CORRECTION

| | |
|---|---|
| PATENT NO. | : 8,170,649 B2 |
| APPLICATION NO. | : 10/587490 |
| DATED | : May 1, 2012 |
| INVENTOR(S) | : Anders Johansson et al. |

Page 1 of 1

It is certified that error appears in the above-identified patent and that said Letters Patent is hereby corrected as shown below:

Claim 25, column 16, line 26, change "two of more" to --two or more--.

Signed and Sealed this
Fourteenth Day of August, 2012

David J. Kappos
*Director of the United States Patent and Trademark Office*